United States Patent [19]

Kato et al.

[11] 3,998,876
[45] Dec. 21, 1976

[54] CATALYTIC PROCESS FOR PREPARATION OF UNSATURATED CARBOXYLIC ACIDS

[75] Inventors: Masaaki Kato, Yamaguchi; Hiroshi Sonobe, Otake; Hiromichi Ishii, Otake; Masao Kobayashi, Otake; Kantaro Yamada, Otake, all of Japan

[73] Assignee: Mitsubishi Rayon Co., Ltd., Tokyo, Japan

[22] Filed: Jan. 31, 1975

[21] Appl. No.: 545,905

Related U.S. Application Data

[63] Continuation-in-part of Ser. No. 407,571, Oct. 18, 1973, abandoned.

[30] Foreign Application Priority Data

Aug. 16, 1973  Japan ............................ 48-91976

[52] U.S. Cl. ........................... 260/530 N; 252/435; 252/437
[51] Int. Cl.² ...................................... C07C 51/32
[58] Field of Search ............... 260/530 N; 252/437, 252/435

[56] References Cited

UNITED STATES PATENTS

| | | | |
|---|---|---|---|
| 3,761,516 | 9/1973 | Khoobear | 260/530 N |
| 3,795,703 | 3/1974 | Niina et al. | 260/530 N |
| 3,875,220 | 1/1975 | White et al. | 260/530 N |

Primary Examiner—Vivian Garner
Attorney, Agent, or Firm—Oblon, Fisher, Spivak, McClelland & Maier

[57] ABSTRACT

The gas phase catalytic oxidation of an unsaturated aldehyde with molecular oxygen at 240° to 390° C to give the corresponding unsaturated carboxylic acid is conducted in the presence of a catalyst represented by the following formula:

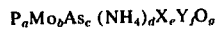

$$P_a Mo_b As_c (NH_4)_d X_e Y_f O_g$$

wherein $a$, $b$, $c$, $e$, $f$ and $g$ represent the atomic ratio of each component and $a$ is 0.03 to 0.2, $b$ is 1, $c$ is 0.015 to 0.15, $e$ is 0.003 to 1, $f$ is 0 to 0.17, $g$ is a value determined by the valencies of the elements present in the catalyst, and $d$ designates the number of ammonium groups which are within the range of 0.01 to 0.3, and wherein X is at least one metal selected from the group consisting of vanadium, tungsten, copper, iron, manganese and tin, and Y is at least one alkali metal element selected from the group consisting of lithium, sodium, potassium, rubidium and cesium. This catalyst is especially effective for the preparation of methacrylic acid from methacrolein, and it has a very long life.

7 Claims, No Drawings under these conditions of c is 0.015 to 0.15, e is 0.003 to 1, f is 0 to 0.17, g is a value determined by the valencies of the elements present in the composition, and d designates the number of ammonium groups which range from 0.01 to 0.3, and wherein X is at least one metal selected from the goup consisting of vanadium, tungsten, copper, iron, manganese

CATALYTIC PROCESS FOR PREPARATION OF UNSATURATED CARBOXYLIC ACIDS

CROSS-REFERENCE TO RELATED APPLICATIONS

This application is a continuation-in-part application of application Ser. No. 407,571, filed Oct. 18, 1973, now abandoned.

BACKGROUND OF THE INVENTION

1. Field of the Invention

This invention relates to a process for preparing unsaturated carboxylic acids from unsaturated aldehydes in the presence of a phosphorous-molybdenum-arsenic catalyst which contains an ammonium group.

2. Description of the Prior Art

Various catalysts have been known as catalysts for the gas phase catalytic oxidation of unsaturated aldehydes such as those disclosed in U.S. Pat. Nos. 3,475,488; 3,567,773; 3,646,127; 3,649,684; 3,686,294 and DT 2,251,364. Included among these catalysts are molybdenum-vanadium catalysts which exhibit excellent effects in the oxidation of acrolein. However, these catalysts are not suitable for the oxidation of methacrolein. Phosphorus-molybdenum-arsenic catalysts of specific compositions give good results in the oxidation of methacrolein. However, these catalysts are still insufficient because some problems remain to be solved, for instance, these catalysts have a very short life. Other types of catalysts do not give good results in the oxidation of methacrolein.

A need, therefore, continues to exist for a catalyst for the oxidation of unsaturated aldehydes such as acrolein and methacrolein to the corresponding unsaturated acids which exhibits excellent catalytic effects and which has a good life time.

SUMMARY OF THE INVENTION

Accordingly, one object of this invention is to provide a process for preparing unsaturated carboxylic acids, especially methacrylic acid, in high yield from unsaturated aldehydes, especially methacrolein.

Another object of this invention is to provide a catalyst having a long life which gives unsaturated carboxylic acids in high yield when used for the catalytic oxidation of unsaturated aldehydes.

Briefly, these objects and other objects of the invention as hereinafter will become more readily apparent can be attained by a process for the preparation of unsaturated carboxylic acids, which comprises catalytically oxidizing an unsaturated aldehyde in the gas phase at a temperature of 240 to 390° C with molecular oxygen to form the corresponding unsaturated carboxylic acid, wherein the catalytic oxidation is performed in the presence of a catalyst having a composition represented by the following formula:

$P_a Mo_b As_c (NH_4)_d X_e Y_f O_g$, wherein a, b, c, e, f and g represent the atomic ratio of each component and a is 0.03 to 0.2, b is 1, c is 0.015 to 0.15, e is 0.003 to 1, f is 0 to 0.17, g is a value determined by the valencies of the elements present in the composition, and d designates the number of ammonium groups which range from 0.01 to 0.3, and wherein X is at least one metal selected from the goup consisting of vanadium, tungsten, copper, iron, manganese and tin, and Y is at least one alkali element selected from the group consisting of lithium, sodium, potassium, rubidium and cesium. Elements of the group X are essential to the composition, while elements of the group Y are optional.

DESCRIPTION OF THE PREFERRED EMBODIMENTS

The atomic ratio of each component in the catalyst used in this invention is critical, and if the atomic ratios are outside the specified ranges, catalysts having the desired properties cannot be obtained. The amount of metal element X in the composition previously shown can be chosen within a range, expressed in terms of the atomic ratio to molybdenum, of from 0.003 to 1. When an element selected from vanadium, tungsten, copper, iron and manganese is used as the metal X, it is preferred that the atomic ratio of the metal X to molybdenum be within the range of from 0.003 to 0.25, especially 0.006 to 0.2. When two or more of these metals are present, it is preferred that the sum of the atomic ratio of the metals to molybdenum be within the above range. If the atomic ratio is below this range, a sufficient catalytic effect cannot be obtained. If the atomic ratio is above this range, the catalyst life is further prolonged but the selectivity to unsaturated acid product is decreased. When tin is used as the metal X, it is preferred that the atomic ratio of the metal to molybdenum be within the range of 0.003 to 1, especially 0.006 to 0.5. In the instance when tin and a metal selected from vanadium, tungsten, copper, iron and manganese are used in combination as the metal component X, it is preferred that the sum of the atomic ratio of tin and the other metal be within the range of 0.003 to 1, especially 0.01 to 0.5 and that the atomic ratio of the metal other than tin to molybdenum be less than 0.25, especially less than 0.2. If tin alone is employed as the metal X, even when it is present in the composition in relatively large amounts as compared to the case when tin is used with the other metal, there is not much reduction in the selectivity to the unsaturated carboxylic acid product. Therefore, substantial improvement in the life of the catalyst can be expected. Among the metal elements represented by X, copper is the most preferred.

The amount of the alkali metal component represented by Y in the catalyst composition is selected to be within the range, expressed in terms of the atomic ratio to molybdenum, of from 0 to 0.17, especially from 0.001 to 0.12. If the amount of the alkali metal Y is greater than this range, a reduction in the selectivity to unsaturated acid product is observed.

In the catalyst of this invention, it is believed that the ammonium group is present in the form of a salt. The ammonium group is incorporated in the catalyst in the amount of 0.01 to 0.3 molecule per atom of molybdenum, preferably 0.01 to 0.2 molecule.

The chemical state of each component element in the catalyst of this invention is very complicated, and the chemical state of each component element in the catalyst has not been completely elucidated. However, it is believed that each component is not simply present in the form of a mere oxide but rather is in the form of a heteropoly-acid compound and the ammonium group is present in the form of a salt of said heteropoly-acid. In this invention, preferably not all of the heteropoly-acid in the catalyst is combined with the ammonium group as a salt, because when this happens, the intended reaction does not proceed. In contrast, if each component of the catalyst is present as the free heteropoly-acid and not as an ammonium salt, the anion structure of the heteropoly-acid rapidly decomposes to the oxide while the oxidation proceeds at a temperature exceeding 300° C and the activity of the catalyst is decreased. In this case, the ability of the catalyst to remove a hydrogen atom from the unsaturated aldehyde is reduced and a catalyst having a high activity cannot be obtained. However, if the heteropoly-acid which has a proton-donating ability and the ammonium salt thereof are present together in the catalyst, the anion structure can be maintained more stably in the heteropoly-acid than in the case where only the heteropoly-acid is present in the catalyst with the result that the selectivity to unsaturated acid product is improved and simultaneously the catalyst life can be prolonged.

When a metal element represented by X is incorporated in the catalyst composed of molybdenum, phosphorus, arsenic, an ammonium group and oxygen, the catalyst life can be substantially improved. The reason has not been completely elucidated, but in view of the known fact that in a molybdenum-containing catalyst, when the concentration of adsorbed oxygen is lowered, the activity and selectivity are reduced, the concentration of adsorbed oxygen is heightened by the presence of the element X and hence, the activity is elevated and the catalyst life is prolonged.

The catalyst of this invention is heat-treated at a temperature of 300° to 440° C before it is used in the oxidation reaction. A preferred heat treatment temperature is within the range of from 360° to 430° C. If the heat treatment temperature exceeds 440° C, both the activity and selectivity of the catalyst are reduced. If the heat treatment temperature exceeds 460° C, the reduction in the selectivity to the desired product becomes very conspicuous. Thus, there is a definite upper limit on the heat treatment for the catalyst of the invention. On the other hand, the lower heat treatment temperature limit is not as critical. However, at heat treatment temperatures not exceeding about 300° C, it is difficult to obtain a catalyst having stable properties. The heat treatment time varies depending on the heat treatment temperature, but in general, it is preferred that the heat treatment be conducted for 30 minutes to several days. It is desired that the heat treatment be conducted in air or air diluted with an inert gas. If necessary, a heat treatment atmosphere of air containing a reducing substance at low concentrations can be used.

The preparation of the catalyst to be used in this invention can be accomplished according to methods known to those skilled in the art. It is desired that the starting materials be intimately mixed with one another, but the method of mixing is not particularly critical. Irregular distribution of the components of the composition can be avoided, by any of the conventional methods such as evaporation-to-dryness, precipitation, oxide-mixing or the like.

Suitable starting materials for the catalyst include ammonium compounds such as ammonium molybdate, ammonium phosphate, ammonium phosphomolybdate, ammonium arsenomolybdate, or the like. Elements represented by X are used as the oxides, nitrates, ammonium salts or the like, and the alkali elements represented by Y are used as the oxides, nitrates, hydroxides or the like.

When catalyst components are used in the form of ammonium salts such as mentioned above, the introduction of the ammonium group into the catalyst is simultaneously achieved. If the ammonium salts are not employed as the starting materials, aqueous ammonia is preferably employed. For instance, a homogeneous mixture can be obtained by dissolving a once-used phosphorus-molybdenum-arsenic catalyst in aqueous ammonia and adding other metal components to the resulting solution for the preparation of this invention.

A catalyst containing ammonium groups can be obtained by drying a homogeneous mixture of starting materials and then heat treating the mixture at a temperature of 300° to 440° C for 30 minutes to several days. The amount of the ammonium group incorporated in the catalyst is 0.01 to 0.3 molecule per atom of molybdenum.

In another method for introducing the ammonium group into the catalyst, a deactivated catalyst is treated with ammonia or aqueous ammonia. For instance, when a catalyst deactivated by use at high temperatures or by use for long times is treated in a reaction vessel with liquid or gaseous aqueous ammonia, a prescribed amount of the ammonium group can be introduced.

The type of a reaction vessel in which the catalyst of the invention is packed is not particularly critical, and either a fixed bed or a fluidized bed reactor can be used in this invention.

Suitable unsaturated aldehydes which can be oxidized in the process of this invention include acrolein, methacrolein, and mixtures of acrolein and methacrolein. The process of this invention is especially effective for the oxidation of methacrolein. Methacrolein which is obtained by the catalytic oxidation of isobutylene or tertiary butanol can be used as it is or after it has been purified.

The concentration of the unsaturated aldehyde in the feed gas can be varied within a broad range, but it is generally preferred that the concentration of the unsaturated aldehyde be within the range of from 1 to 20% by volume, especially 3 to 15% by volume. Molecular oxygen is used as the oxidant in the process of this invention. Preferably, air is used from an economic viewpoint. If necessary, an oxidant of air enriched with pure oxygen can also be used. Preferably, the concentration of oxygen in the feed gas, expressed in terms of the mole ratio to the unsaturated aldehyde, is within the range of 0.3 to 4, especially 0.4 to 2.5. The starting gaseous mixture may be diluted with an inert gas such as nitrogen, steam, carbon dioxide or the like.

The oxidation reaction is conducted under a pressure ranging from atmospheric pressure to several atmospheres. The space velocity of the feed gas varies depending on the reaction temperature and pressure, but it is generally preferred that the starting gaseous mixture be fed at a space velocity of 300 $hr^{-1}$ to 10,000 $hr^{-1}$. The reaction temperature is chosen within a range of from 240° to 390° C, but it is generally preferred that the reaction temperature range from 270° to 340° C. One of the characteristic features of this invention is that the oxidation reaction can be performed at such relatively low temperatures.

Having generally described this invention, a further understanding can be obtained by reference to certain specific examples which are provided herein for purposes of illustration only and are not intended to be limiting unless otherwise specified. In the Examples, the term "parts" is by weight and the selectivity to the unsaturated carboxylic acid is expressed in terms of the ratio (percent) of the molar amount of the unsaturated carboxylic acid product to the molar amount of the reacted unsaturated aldehyde. The reaction time was measured from the point when the reaction conditions described in the Examples were actually established.

EXAMPLE 1

177 Parts of ammonium paramolybdate were dissolved in 500 parts of pure water maintained at about 60° C, and 9.6 parts of 85% phosphoric acid and 10.5 parts of a 50% aqueous solution of arsenic acid were added to the solution. Then, a solution of 4.88 parts of ammonium metavanadate in 150 parts of water were added to the mixture. The resulting mixed solution was evaporated to dryness by heating with agitation, and the resulting solid was dried at 150° C for 16 hours. The resulting dried solid was pulverized in a ball mill, compression-molded, placed in an electric furnace and heat-treated. The heat treatment was performed by elevating the temperature from 100° C to 400° C at a rate of 20° C per hour, and then maintaining the solid at 400° C for 16 hours. The catalyst so obtained contained the phosphorus and metal components in the following atomic ratio:

$Mo_1P_{0.083}As_{0.037}V_{0.042}(NH_4)_{0.078}$

This catalyst was packed in a fixed bed reaction vessel and maintained at 295° C, and a gaseous mixture comprising 5% by volume methacrolein, 5% by volume oxygen, 20% by volume steam and 70% by volume nitrogen was fed into the reaction vessel at a space velocity of 2000 hr$^{-1}$. Under these conditions, the reaction was conducted for a long time. At prescribed intervals the reaction gas discharged from the reaction vessel was sampled and analyzed by gas chromatography or the like to determine the activity of the catalyst. Results are shown in Table I.

TABLE I

| Reaction Time (hours) | Conversion of Methacrolein (%) | Selectivity to Methacrylic Acid (%) |
| --- | --- | --- |
| 4 | 57.1 | 84.9 |
| 240 | 58.0 | 85.2 |
| 480 | 57.7 | 85.5 |
| 960 | 57.5 | 85.8 |
| 1440 | 55.9 | 85.0 |

EXAMPLE 2

The oxidation of acrolein was conducted with the use of the catalyst prepared in Example 1. The starting gaseous mixture comprised 5% by volume acrolein, 5% by volume oxygen, 20% by volume steam and 70% by volume nitrogen. The reaction temperature was adjusted to 300° C. The other operational procedures and conditions were the same as those described in Example 1. Results of the experiment are summarized in Table II.

TABLE II

| Reaction Time (hours) | Conversion of Acrolein (%) | Selectivity to Acrylic Acid (%) |
| --- | --- | --- |
| 4 | 55.3 | 86.9 |
| 240 | 56.1 | 87.2 |
| 480 | 55.9 | 87.5 |
| 960 | 56.0 | 87.0 |
| 1440 | 55.1 | 86.7 |

EXAMPLE 3

A catalyst was prepared in the same manner as described in Example 1 except that the aqueous arsenic acid solution was changed to 4.95 parts or arsenous anhydride, the aqueous solution of ammonium metavanadate was changed to a solution of 3.37 parts of ferric nitrate in 50 parts of water, and the heat treatment conditions were changed in such a manner that the maximum temperature was 380° C and the period during which this maximum temperature was maintained was 24 hours. The atomic ratios of the phosphorus and metal components in the resulting catalyst were as follows:

$Mo_1P_{0.083}As_{0.05}Fe_{0.0083}(NH_4)_{0.125}$

With the use of the thus obtained catalyst, the oxidation of methacrolein was conducted under the same conditions as described in Example 1 except that the reaction temperature was changed to 305° C whereby the results shown in Table III were obtained.

TABLE III

| Reaction Time (hours) | Conversion of Methacrolein (%) | Selectivity to Methacrylic Acid (%) |
| --- | --- | --- |
| 4 | 48.9 | 84.0 |
| 240 | 50.2 | 86.3 |
| 480 | 50.0 | 86.5 |
| 960 | 50.1 | 86.0 |

EXAMPLES 4 to 7

Catalysts were prepared in the same manner as described in Example 1 except that the ammonium metavanadate used in Example 1 was changed to ammonium paratungstate or manganese nitrate and in some Examples the amount of arsenic acid added, the maximum heat treatment temperature and/or the maximum temperature-maintaining time was changed as indicated in Table IV.

Oxidation of methacrolein or acrolein was conducted with the thus obtained catalysts under the same conditions as described in Example 1 or 2 except that the reaction temperature was changed as indicated in Table IV.

Catalysts, reaction conditions and experimental results are summarized in Table IV.

TABLE IV

| Example No. | Catalyst Composition (atomic ratio) | Heat Treatment Temperature (°C) | Heat Treatment Time (hours) | Oxidation Starting Aldehyde | Temperature (°C) | Time (hours) | Conversion (%) | Selectivity (%) |
|---|---|---|---|---|---|---|---|---|
| 4-1 | $Mo_1P_{0.083}As_{0.025}Cu_{0.083}(NH_4)_{0.14}$ | 370 | 48 | acrolein | 300 | 4 | 59.4 | 85.3 |
|  |  |  |  |  |  | 960 | 58.8 | 85.7 |
| 4-2 | '' | '' | '' | methacrolein | 286 | 4 | 54.0 | 84.6 |
|  |  |  |  |  |  | 960 | 55.3 | 85.5 |
| 4-3 | $Mo_1P_{0.083}As_{0.05}Cu_{0.0208}(NH_4)_{0.094}$ | 385 | 12 | acrolein | 330 | 4 | 93.2 | 91.0 |
|  |  |  |  |  |  | 960 | 93.0 | 91.5 |
| 4-4 | '' | '' | '' | methacrolein | 315 | 4 | 95.9 | 85.9 |
| 4-5 | '' | '' | '' | methacrolein* | 290 | 960 | 95.5 | 85.0 |
|  |  |  |  |  |  | 960 | 95.0 | 84.0 |
| 4-6 | $Mo_1P_{0.083}As_{0.05}Cu_{0.0416}(NH_4)_{0.106}$ | 380 | 12 | acrolein | 300 | 4 | 75.0 | 92.1 |
|  |  |  |  |  |  | 960 | 75.5 | 92.0 |
| 4-7 | '' | '' | '' | methacrolein | 300 | 4 | 75.4 | 89.5 |
|  |  |  |  |  |  | 960 | 76.0 | 89.7 |
| 5 | $Mo_1P_{0.058}As_{0.05}W_{0.0083}(NH_4)_{0.086}$ | 400 | 10 | methacrolein | 288 | 4 | 48.2 | 85.6 |
|  |  |  |  |  |  | 960 | 49.7 | 86.0 |
| 6 | '' | '' | '' | acrolein | 295 | 4 | 47.0 | 88.2 |
|  |  |  |  |  |  | 960 | 47.3 | 88.2 |
| 7 | $Mo_1P_{0.083}As_{0.075}Mn_{0.167}(NH_4)_{0.033}$ | 410 | 8 | methacrolein | 310 | 4 | 52.5 | 84.2 |
|  |  |  |  |  |  | 960 | 52.4 | 85.0 |

*space velocity of 500 hr$^{-1}$

COMPARATIVE EXAMPLE 1

An experiment was conducted in which methacrolein was oxidized over a catalyst having the same composition of Example 4-3 except that it was supported on an Alundum carrier (Norton Co., Ltd. - Cat. No. SA 5205) having the following composition: 84.7 wt% $Al_2O_3$; 13.4 wt% $SiO_2$; 0.2 wt% $Fe_2O_3$; 0.3 wt% $TiO_2$; 0.02 wt% CaO; 0.04 wt% MgO; 0.60 wt% $Na_2O$ and 0.7 wt% $K_2O$. The carrier has the following characteristics:

| | |
|---|---|
| Apparent Porosity | 55–61% |
| Coefficient of Water Absorption | 37–43% |
| Apparent Specific Gravity | 1.4–1.6 |
| Specific Gravity | 3.3–3.6 |
| Filling density | 800–896 Kg/m$^3$ |
| Pore diameter | 50–1500μ |
| Surface area | < 1m$^2$/g |

The weight ratio of carrier to catalyst component was 68:32. Note that the Alundum support has a pore diameter ranging from 50 – 1500μ and a surface area of <1m$^2$/g which overlap the respective ranges required by the catalyst support of Khoobiar, U.S. Pat. No. 3,761,516, i.e., a surface area of at most 2 m$^2$/g and pore diameters ranging from 1 – 500μ.

The supported catalyst was prepared by placing the concentrated and dried catalyst of Example 4-3 in an electric furnace wherein the temperature was elevated at a rate of 20° C/hr under a flow of air. The temperature of the furnace was maintained at 300° C for 2 hours. The heated material was crushed and mixed. Seventy parts by weight of the crushed catalyst was added to water and pulverized to form a slurry. One hundred thirty parts by weight of the above Alundum carrier was mixed with the catalyst slurry by placing the carrier on a rotational drier and spraying the carrier with the catalyst slurry at 120° C, thereby impregnating the carrier with the catalyst. The resulting catalyst was subjected to heat treatment under a flow of air in an electric furnace at 385° C for 12 hours. The temperature of the furnace was elevated at a rate of 20° C/hr.

The resulting supported catalyst as a catalyst system consistent with the supported catalyst of Khoobiar was exposed to a gaseous feed mixture of 5 vol% methacrolein, 5 vol% oxygen, 20 vol% steam and 70 vol% nitrogen at a space velocity of 2000 hr$^{-1}$. The results of the oxidation of methacrolein are shown in Table V below.

TABLE V

| Reaction time hr | Reaction temperature °C | Conversion % | Selectivity % |
|---|---|---|---|
| 4 | 300 | 25.8 | 85.0 |
| 12 | 330 | 45.0 | 83.0 |
| 240 | 330 | 35.0 | 82.0 |

The results of Table V when compared with the results in Table IV for Example 4-4 show clearly that the non-supported catalyst of the present invention exhibits a much higher degree of conversion than the supported catalyst at comparable selectivities. Further, after 960 hrs. of operation, the non-supported catalyst of the present invention shows the same degree of methacrolein conversion while the conversion data for the supported catalyst after only 240 hours of operation has diminished significantly.

EXAMPLE 8

204 Parts of phosphomolybdic acid ($P_2O_5\cdot2\text{-}4MoO_3\cdot72H_2O$) were dissolved in 500 parts of pure water, and 4.8 parts of arsenous anhydride was added to the solution. Then, 75.0 parts of fine powder of stannic oxide were further added to the solution. Under agitation the resulting suspension was added to 150 parts of 28% aqueous ammonia, and the resulting mixture was evaporated to dryness by heating. Subsequent procedures were conducted in the same manner as described in Example 1, and in the final stage the heat treatment was conducted at 400° C for 16 hours to obtain a catalyst. The atomic ratio of the phosphorus and metal components in the resulting catalyst was as follows:

$Mo_1P_{0.083}As_{0.049}Sn_{0.5}(NH_4)_{0.062}$

With the use of this catalyst, the oxidation of methacrolein was conducted under the same conditions as described in Example 1 except that the reaction temperature was changed to 320° C whereby the results shown in Table VI were obtained.

TABLE VI

| Reaction Time (hours) | Conversion of Methacrolein (%) | Selectivity to Methacrylic Acid (%) |
|---|---|---|
| 4 | 78.9 | 84.1 |
| 480 | 81.3 | 85.2 |
| 960 | 81.1 | 85.6 |

EXAMPLE 9

With the use of the catalyst prepared in Example 8, the oxidation of acrolein was conducted under the same conditions as described in Example 2 except that the reaction temperature was changed to 325° C, whereby the results shown in Table VII were obtained.

TABLE VII

| Reaction Time (hours) | Conversion of Acrolein (%) | Selectivity to Acrylic Acid (%) |
|---|---|---|
| 4 | 83.4 | 85.9 |
| 480 | 83.2 | 86.2 |
| 960 | 84.0 | 86.0 |

EXAMPLES 10 to 12

Catalysts were prepared in the same manner as described in Example 1 except that the amount of ammonium metavanadate added was changed to 2.94 parts and, after the addition of ammonium metavandate, 3.37 parts of ferric nitrate, 2.24 parts of ammonium paratungstate or 23.1 parts of manganese nitrate in 50 parts of pure water was further added.

With the use of these catalysts, the oxidation of methacrolein was conducted under the same conditions as described in Example 1 except that the reaction temperature was changed as indicated in Table VIII. Catalysts, reaction conditions and experimental results are summarized in Table VIII.

TABLE VIII

| Example No. | Composition of Catalyst (atomic ratio) | Reaction Temperature (° C) | Reaction Time (hours) | Conversion of Methacrolein (%) | Selectivity to Methacrylic Acid (%) |
|---|---|---|---|---|---|
| 10 | $Mo_1P_{0.083}As_{0.037}V_{0.025}Fe_{0.0083}(NH_4)_{0.101}$ | 295 | 4 | 52.6 | 83.9 |
|  |  |  | 1440 | 53.0 | 84.5 |
| 11 | $Mo_1P_{0.083}As_{0.037}V_{0.025}W_{0.0083}(NH_4)_{0.078}$ | 285 | 4 | 50.0 | 84.3 |
|  |  |  | 1440 | 51.1 | 84.3 |
| 12 | $Mo_1P_{0.083}As_{0.037}V_{0.025}Mn_{0.083}(NH_4)_{0.11}$ | 300 | 4 | 47.2 | 83.6 |
|  |  |  | 1440 | 47.0 | 83.7 |

EXAMPLES 13 to 17

Catalyst were prepared in the same manner as described in Example 1 except that the ammonium metavanadate used in Example 1 was changed to ammonium paratungstate, and after the addition of ammonium paratungstate, an aqueous solution of a nitrate of copper, iron or manganese was further added. The atomic ratio of arsenic and the heat treatment conditions were somewhat changed as indicated in Table IX.

With the use of these catalysts, the oxidation of methacrolein or acrolein was conducted under the same conditions as described in Example 1 or 2 except that the reaction temperature was changed as indicated in Table IX. Catalysts, oxidation conditions and results are summarized in Table IX.

TABLE IX

| | Catalyst | | | Oxidation Conditions | | | Results | |
|---|---|---|---|---|---|---|---|---|
| Example No. | Composition (atomic ratio) | Heat Treatment Temperature (° C) | Heat Treatment Time (hours) | Starting Aldehyde | Temperature (° C) | Time (hours) | Conversion (%) | Selectivity (%) |
| 13 | $Mo_1P_{0.083}As_{0.05}W_{0.0083}Cu_{0.017}(NH_4)_{0.075}$ | 400 | 16 | methacrolein | 300 | 4 | 59.3 | 82.6 |
|  |  |  |  |  |  | 1440 | 58.7 | 83.0 |
| 14 | " | 400 | 16 | acrolein | 310 | 4 | 54.7 | 86.1 |
|  |  |  |  |  |  | 1440 | 55.0 | 86.5 |
| 15 | $Mo_1P_{0.083}As_{0.05}W_{0.0083}Fe_{0.042}(NH_4)_{0.044}$ | 410 | 8 | methacrolein | 295 | 4 | 55.5 | 84.7 |
|  |  |  |  |  |  | 1440 | 55.4 | 84.3 |
| 16 | $Mo_1P_{0.083}As_{0.05}W_{0.0083}Mn_{0.083}(NH_4)_{0.111}$ | 380 | 24 | methacrolein | 310 | 4 | 59.7 | 84.2 |
|  |  |  |  |  |  | 1440 | 60.0 | 83.9 |
| 17 | " | 380 | 24 | acrolein | 310 | 4 | 54.0 | 85.9 |
|  |  |  |  |  |  | 1440 | 54.7 | 85.4 |

EXAMPLES 18 to 21

204 Parts of phosphomolybdic acid were dissolved in 500 parts of pure water, and 28.2 parts of a 50% aqueous solution of arsenic acid was added thereto. Then, a solution of 10.1 parts of ferric nitrate in 50 parts of pure water was added to the above solution, and 25.0 parts of a fine powder of stannic oxide was further added thereto. The resulting suspension was added with agitation to 150 parts of 28% aqueous ammonia, and the mixture was evaporated to dryness by heating. Subsequent procedures were conducted in the same manner as described in Example 1, and in the final stage, the heat treatment was conducted at 400° C for 5 hours, whereby a catalyst containing iron and tin was obtained.

Catalysts containing tin and tungsten, vanadium or manganese were prepared in the same manner as described above except that ferric nitrate was replaced with ammonium paratungstate, ammonium metavanadate or manganese nitrate.

With the use of the thus prepared catalysts, the oxidation of methacrolein or acrolein was conducted under the same conditions as described in Example 1 or 2 except that the reaction temperature was changed as indicated in Table X. Catalysts, oxidation conditions and experimental results are summarized in Table X.

COMPARATIVE EXAMPLES 2 and 3

A catalyst was prepared in the same manner as described in Example 1 except that ammonium metavanadate was not added at all. With the use of this catalyst, the oxidation of methacrolein or acrolein was conducted under the same conditions as described in Example 1 or 2 except that the reaction temperature was changed to 300° C. The results are summarized in Table XII.

TABLE X

| | Catalyst | | | Oxidation | | | Results | |
|---|---|---|---|---|---|---|---|---|
| Example No. | Composition (atomic ratio) | Heat Treatment Temperature (°C) | Heat Treatment Time (hours) | Starting Aldehyde | Reaction Temperature (°C) | Reaction Time (hours) | Conversion (%) | Selectivity (%) |
| 18 | $Mo_1P_{0.083}As_{0.1}Sn_{0.17}Fe_{0.025}(NH_4)_{0.023}$ | 400 | 5 | methacrolein | 305 | 4 | 61.2 | 85.3 |
| | | | | | | 1440 | 61.3 | 85.2 |
| 19 | $Mo_1P_{0.083}As_{0.1}Sn_{0.17}W_{0.0083}(NH_4)_{0.034}$ | 400 | 5 | acrolein | 310 | 4 | 53.9 | 87.0 |
| | | | | | | 1440 | 54.2 | 86.8 |
| 20 | $Mo_1P_{0.083}As_{0.1}Sn_{0.17}V_{0.017}(NH_4)_{0.036}$ | 400 | 5 | methacrolein | 305 | 4 | 59.9 | 87.0 |
| | | | | | | 1440 | 59.6 | 87.3 |
| 21 | $Mo_1P_{0.083}As_{0.1}Sn_{0.17}Mn_{0.042}(NH_4)_{0.03}$ | 400 | 5 | acrolein | 315 | 4 | 54.3 | 86.0 |
| | | | | | | 1440 | 56.5 | 86.2 |

EXAMPLES 22 to 26

Catalysts were prepared in the same manner as described in Example 1 except that the ammonium metavanadate used in Example 1 was replaced with copper nitrate, and, after the addition of an aqueous solution of copper nitrate, an aqueous solution of lithium nitrate, sodium nitrate, potassium nitrate, rubidium nitrate or cesium nitrate was added. In some Examples, the amount of arsenic acid added, the maximum heat treatment temperature and/or the maximum temperature-maintaining time was changed as indicated in Table XI.

With the use of the thus prepared catalysts, the oxidation of methacrolein or acrolein was conducted under the same conditions as described in Example 1 or 2 except that the reaction temperature was changed as indicated in Table XI. Catalysts, oxidation conditions and experimental results are summarized in Table XI.

TABLE XII

| Comparative Example No. | Starting Aldehyde | Reaction Time (hours) | Conversion (%) | Selectivity (%) |
|---|---|---|---|---|
| 2 | methacrolein | 4 | 55.0 | 85.5 |
| | | 120 | 54.6 | 84.2 |
| | | 240 | 55.2 | 85.3 |
| | | 480 | 52.1 | 83.7 |
| 3 | acrolein | 4 | 49.3 | 87.2 |
| | | 120 | 48.4 | 87.0 |
| | | 240 | 48.7 | 86.5 |
| | | 480 | 46.2 | 86.9 |

As is apparent from the results obtained with the comparative catalyst as shown in Table XII, a tendency was observed for a reduction in the conversion or both the conversion and the selectivity to some extent after 480 hours had passed from the initiation of the reaction. In contrast, it is apparent from the results shown in Tables I to IV and II to XI, in the instances of catalysts containing at least one member selected from vanadium, tungsten, copper, iron, manganese and tin, and optionally an alkali metal element, such a tendency

TABLE XI

| | Catalyst | | | Oxidation Conditions | | | Results | |
|---|---|---|---|---|---|---|---|---|
| Example No. | Composition (atomic ratio) | Heat Treatment Temperature (°C) | Heat Treatment Time (hours) | Starting Aldehyde | Reaction Temperature (°C) | Reaction Time (hours) | Conversion (%) | Selectivity (%) |
| 22 | $Mo_1P_{0.083}As_{0.025}Cu_{0.025}Li_{0.025}(NH_4)_{0.125}$ | 380 | 8 | methacrolein | 300 | 4 | 89.5 | 87.9 |
| | | | | | | 1440 | 89.4 | 90.1 |
| 23-1 | $Mo_1P_{0.083}As_{0.067}Cu_{0.05}Na_{0.025}(NH_4)_{0.155}$ | 370 | 10 | methacrolein | 280 | 4 | 95.2 | 88.5 |
| | | | | | | 1440 | 95.6 | 88.6 |
| 23-2 | " | " | " | acrolein | 310 | 4 | 90.2 | 91.2 |
| | | | | | | 1440 | 96.0 | 91.3 |
| 24 | $Mo_1P_{0.083}As_{0.025}Cu_{0.025}K_{0.021}(NH_4)_{0.14}$ | 380 | 8 | methacrolein* | 270 | 4 | 94.0 | 88.5 |
| 24-1 | $Mo_1P_{0.083}As_{0.025}Cu_{0.025}K_{0.021}(NH_4)_{0.14}$ | 380 | 8 | methacrolein | 285 | 4 | 93.5 | 89.8 |
| | | | | | | 1440 | 94.0 | 90.1 |
| 24-2 | " | " | " | acrolein | 295 | 4 | 95.3 | 93.3 |
| | | | | | | 1440 | 95.5 | 93.2 |
| 25 | $Mo_1P0.083As_{0.05}Cu_{0.05}Rb_{0.025}(NH_4)_{0.094}$ | 390 | 5 | methacrolein | 305 | 4 | 93.9 | 89.6 |
| | | | | | | 1440 | 94.2 | 89.0 |
| 26 | $Mo_1P0.083As_{0.05}Cu_{0.025}Cs_{0.025}(NH_4)_{0.148}$ | 380 | 5 | methacrolein | 300 | 4 | 93.0 | 89.3 |
| | | | | | | 1440 | 93.3 | 89.4 |

*Space velocity = 500 hr$^{-1}$

What is claimed as new and intended to be covered by letters patent is:

1. A process for the preparation of unsaturated carboxylic acids, which comprises: catalytically oxidizing acrolein, methacrolein or mixtures thereof in the gas phase at a temperature of 240° to 390° C with molecular oxygen to form the corresponding unsaturated carboxylic acid in the presence of a non-carrier supported catalyst having a composition

wherein $a$, $b$, $c$, $e$, $f$ and $g$ represent the atomic ratio of each component and $a$ is within the range of 0.03 to 0.2, $b$ is 1, $c$ is within the range of 0.015 to 0.15, $e$ is within the range of 0.003 to 1, $f$ is within the range of 0 to 0.17, $g$ is a value which is determined by the valences of the elements in the catalyst, and $d$ designates the number of ammonium groups which are within the range of 0.01 to 0.3, and wherein X is at least one metal selected from the group consisting of vanadium, tungsten, copper, iron, manganese, and tin, and Y is at least one alkali metal element selected from the group consisting of lithium, sodium, potassium, rubidium and cesium.

2. The process of claim 1, wherein the catalyst is heat-treated at a temperature of 300° – 440° C.

3. The process of claim 1, wherein the unsaturated aldehyde is methacrolein.

4. The process of claim 1, wherein the metal X is copper.

5. The process of claim 1, wherein the catalyst is composed of a heteropoly-acid of each metal component and an ammonium salt thereof.

6. A process for the preparation of unsaturated carboxylic acids, which comprises: catalytically oxidizing acrolein, methacrolein or mixtures thereof in the gas phase at a temperature of 240° to 390° C with molecular oxygen to form the corresponding unsaturated carboxylic acid in the presence of a non-carrier supported catalyst having a composition

wherein $a$, $b$, $c$, $e$, $f$ and $g$ represent the atomic ratio of each component and $a$ is within the range of 0.03 to 0.2, $b$ is 1, $c$ is within the range of 0.015 to 0.15, $e$ is within the range of 0.003 to 1, $f$ is within the range of 0.001 to 0.12, $g$ is a value which is determined by the degree of oxidation of the catalyst, and $d$ designates the number of ammonium groups which are within the range of from 0.01 to 0.2, and wherein X is at least one metal selected from the group consisting of vanadium, tungsten, copper, iron, manganese and tin, and Y is at least one alkali metal element selected from the group consisting of lithium, sodium, potassium, rubidium and cesium.

7. The process of claim 6, wherein the metal X is copper.

* * * * *

UNITED STATES PATENT AND TRADEMARK OFFICE
CERTIFICATE OF CORRECTION

PATENT NO. : 3,998,876
DATED : Dec. 21, 1976
INVENTOR(S) : Masaaki Kato, et al

It is certified that error appears in the above-identified patent and that said Letters Patent are hereby corrected as shown below:

[75] After "Kantaro Yamada, Otake," insert --Teruhiko Yoshioka, Otake; Hideo Matsuzawa, Otake--

Signed and Sealed this

Twenty-fourth Day of May 1977

[SEAL]

Attest:

RUTH C. MASON
*Attesting Officer*

C. MARSHALL DANN
*Commissioner of Patents and Trademarks*